United States Patent [19]
Heywang-Koebrunner

[11] Patent Number: 5,699,800
[45] Date of Patent: Dec. 23, 1997

[54] STEREOTACTIC EXAMINATION ARRANGEMENT FOR CONDUCTING MAGNETIC RESONANCE EXAMINATIONS

[75] Inventor: Sylvia Heywang-Koebrunner, Engelsdorf, Germany

[73] Assignee: Siemens Aktiengesellschaft, Munich, Germany

[21] Appl. No.: 564,643

[22] Filed: Nov. 29, 1995

[30] Foreign Application Priority Data

Nov. 30, 1994 [DE] Germany ............ 44 42 398.5

[51] Int. Cl.$^6$ .................................................. A61B 5/055
[52] U.S. Cl. ...................... 128/653.2; 324/318; 606/130
[58] Field of Search ...................... 128/653.1, 653.2; 324/318, 322; 606/130; 378/162, 205

[56] References Cited

U.S. PATENT DOCUMENTS

| | | | |
|---|---|---|---|
| 5,178,146 | 1/1993 | Giese | 128/653.2 |
| 5,218,964 | 6/1993 | Sepponen | 128/653.4 |
| 5,394,457 | 2/1995 | Leibinger et al. | |
| 5,433,717 | 7/1995 | Robinsky et al. | 606/20 |
| 5,464,410 | 11/1995 | Skeens et al. | 606/130 |
| 5,483,961 | 1/1996 | Kelly et al. | 128/653.1 |
| 5,588,430 | 12/1996 | Boua et al. | 128/653.1 |
| 5,590,655 | 1/1997 | Hussman | 128/653.1 |

FOREIGN PATENT DOCUMENTS

OS 43 25 206  2/1994  Germany.

*Primary Examiner*—Brian L. Casler
*Attorney, Agent, or Firm*—Hill, Steadman & Simpson

[57] ABSTRACT

A stereotactic auxiliary attachment for magnetic resonance examinations has an antenna arrangement for receiving magnetic resonance signals from an examination space, a holder for fixing an examination subject in the examination space and a marker arrangement in the detection region of the antenna arrangement having at least one chamber for containing a substance to provide a reference for localizing an object of interest in the examination subject. The at least one chamber is connected via lines to a refilling device. The refilling device is provided for filling the at least one chamber with a first substance or second substance, the two substances having different magnetic resonance behavior. The chamber is filled with one substance for production of a first MR tomogram, and this substance is then removed from the chamber and replaced with the second substance for producing a second MR tomogram. Since the substances have different magnetic resonance behavior, the marks in the first and second tomograms remain visible when a subtraction image is produced from those tomograms, so the localization information is not lost.

22 Claims, 1 Drawing Sheet

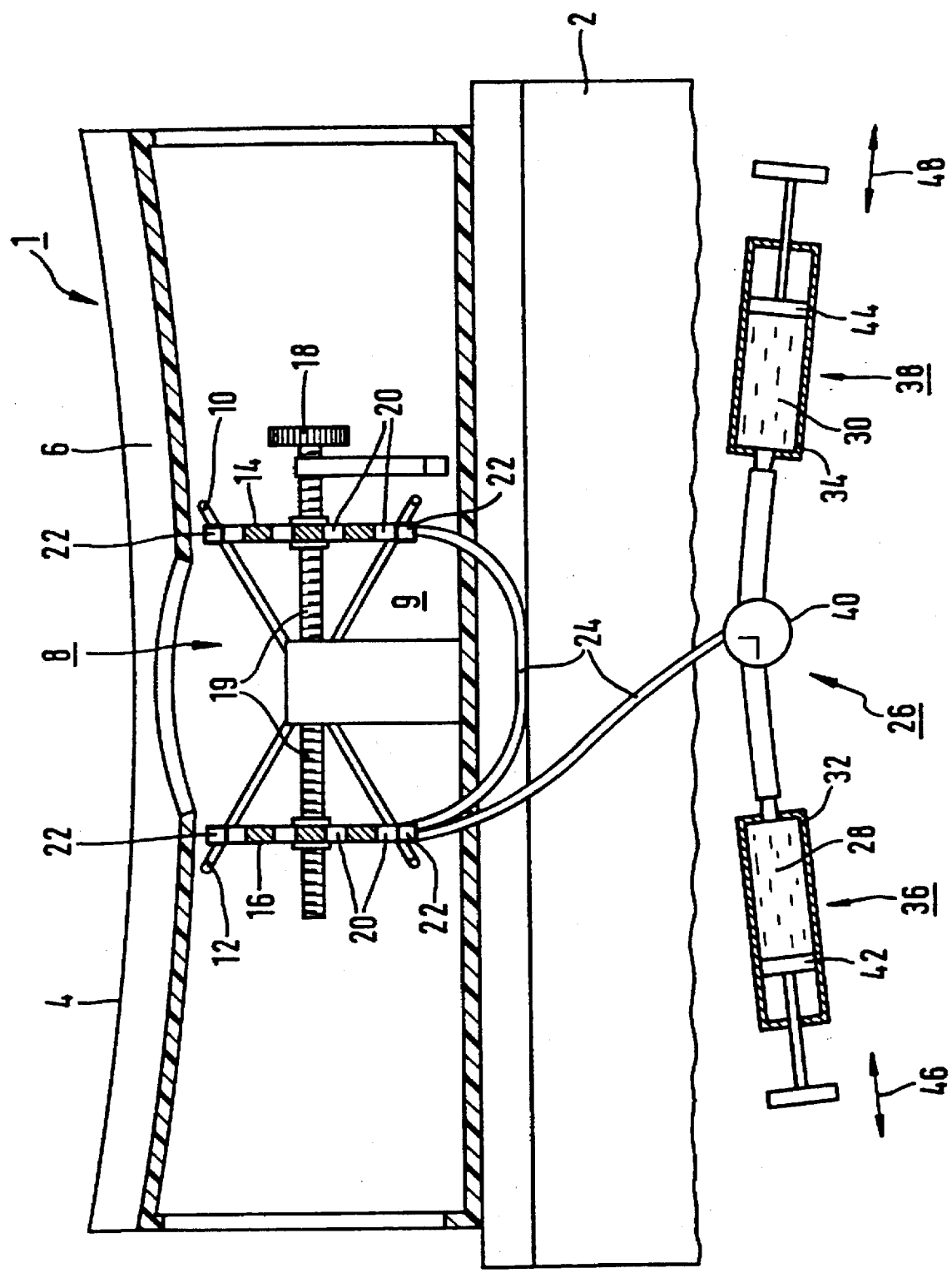

5,699,800

STEREOTACTIC EXAMINATION ARRANGEMENT FOR CONDUCTING MAGNETIC RESONANCE EXAMINATIONS

BACKGROUND OF THE INVENTION

1. Field of the Invention

The invention is directed to a stereotactic examination arrangement for magnetic resonance examinations and in particular to such an examination arrangement in the form of an auxiliary attachment for a magnetic resonance imaging apparatus.

2. Description of the Prior Art

German OS 43 25 206 discloses a stereotactic auxiliary attachment having an antenna arrangement for receiving magnetic resonance signals from an examination space, holder means for fixing an examination subject in the examination space, and marker means that is arranged in the detection region of the antenna arrangement and comprises at least one chamber containing a substance for providing a reference for identifying a location of an object of interest, such as a lesion, in the examination subject. The sterotactic auxiliary attachment disclosed therein has two compression plates arranged parallel and displacable relative to one another between which an examination subject, a female breast, can be fixed. At least one of the compression plates has a reception coil for magnetic resonance signals allocated to it and at least one compression plate has holes for providing a guided access of a biopsy needle to the examination subject. The reception coil has marker means allotted to it that generates marks in the tomogram by means of which lesions visible in the tomogram can be localized.

Important tissue regions in the examination subject can often be diagnosed better in tomograms registered with the administration of a contrast agent. For evaluation, tomograms before and after administration of the contrast agent are subtracted from one another and order to achieve better contrast between the tissue section and its environment. The visibility of the aforementioned localization marks is degraded in the subtraction images since the marks are identical in both tomograms and can cancel in the subtraction image.

In conjunction with medical imaging methods, German Patent 42 33 978 discloses a marking system removably attached to mounts. The marking system contains substances that produce a good image contrast in the particular imaging method employed. When anatomical image data are acquired with various imaging methods from a portion of the human body using the correspondingly adapted marking systems, these images then can be superimposed with the assistance of the imaged marks. This arrangement for generating marks is usable when the patient is successively examined in different types of medical imaging systems. When, however, the patient is examined in only one medical imaging apparatus, such a replacement of marking substances would impede and lengthen the examination. Adding or removing marks between measurements in a magnetic resonance apparatus between measurements before and/or after an intravenous injection of a contrast agent is visually not possible according to the prior art since the patient in many types of magnetic resonance apparatus is not accessible. Interchanging the marking substances must ensue outside of the magnetic resonance apparatus. Additional imprecisions in the imaging of the portion can thereby be caused by patient movements.

SUMMARY OF THE INVENTION

An object of the present invention is to provide a stereotactic auxiliary attachment for a magnetic resonance imaging system which improves the visibility of localization markings in substraction images.

This object is achieved in a stereotactic auxiliary attachment for a magnetic resonance imaging apparatus having a holder for the examination subject, the holder having at least one chamber connected via lines to a refilling means for filling the at least one chamber with a first substrate or with a second substance, the two substances behaving differently in magnetic resonance terms. The interchange of the two substances between the respective exposures of the tomograms before and after administration of the contrast agent enhances the visibility of the marking in the subtraction image. In practice, the tomogram before administration of contrast agent is then produced with the first substance for marking such as, for example, water and the second tomogram after the administration of contrast agent is produced with the second substance for marking such as, for example, gadolinium-DTPA.

DESCRIPTION OF THE DRAWINGS

The single figure is a front view, partly in section, of a stereotactic auxiliary attachment for conducting a magnetic resonance imaging examination constructed in accordance with the principles of the present invention.

DESCRIPTION OF THE PREFERRED EMBODIMENTS

The stereotactic auxiliary attachment 1 shown in a frontal sectional view is fashioned for conducting a magnetic resonance examination of a female breast with the patient in a prone position. Magnetic resonance tomograms (MR tomograms) of the breast are thereby produced. The auxiliary attachment 1 is disclosed in detail in the above-cited German OS 43 25 206 (which corresponds to U.S. application Ser. No. 08/098,828 filed Jul. 29, 1993, "Stereotactic Attachment for a Nuclear Magnetic Imaging Apparatus," Heywang-Koebrunner, the teachings of which are incorporated herein by reference), so that the description thereof is limited here to the basic aspects. The auxiliary attachment 1 is fashioned in the form of a superstructure of a patient bed 2. The auxiliary attachment has a housing 4 (shown in section) whose upper side serves as a surface 6 for the patient to lie on. An opening 8 that is provided for the acceptance of the breast, and thus forms the access of the examination subject to an examination space 9, is provided in this bed surface 6. The examination space 9 is defined by an antenna arrangement that encompasses two conductor loops 10 and 12 arranged crossed. The crossed antenna loops 10 and 12 are provided for the reception of circularly polarized magnetic resonance signals from the examination space 9.

For fixing the breast, two compression plates 14 and 16 arranged parallel to each other are provided as retainer means that can be oppositely adjusted via a handwheel 18 with the assistance of an opposed thread 19.

The two compression plates 14 and 16 are provided with through-holes 20 that enable a guided access of biopsy needles to the examination subject from the outside. Only a few through-holes 20 are shown; in fact, the through-holes 20 are present in the compression plates 14 and 16 in a grid with spacings between neighboring through-holes of, for example, 2.5 mm.

The compression plates 14 and 16 are rectangular, and a chamber 22 fashioned as a tube is arranged in each compression plate 14 and 16 proceeding around the edge. The chamber 22 is part of a marking means that lies in the detection region of the antenna arrangement formed by loops 10 and 12. The chambers 22 can be filled with a liquid or gaseous substance visible in the tomogram that is also suitable for interchanging (i.e., it is (if a liquid) not viscous and does not leave a significant residue when removed or flushed out from the chambers 22).

The chambers 22 are connected to one another and to a refilling device 26 via hose-like lines 24. The refilling device 26 serves the purpose of filling the chambers 22 with a first substance 28 or with a second substance 30 (one at a time). The two substances behave differently in magnetic resonance terms, i.e. they are reproduced with different brightnesses in an MR tomogram. For example, water may be provided as the first substance 28 and a liquid enriched with a contrast agent such as, for example, gadolinium-DTPA or copper sulfate may be provided as the second substance 30.

Respective reservoirs 32 and 34 for the two substances 28 and 30 are provided in the refilling device 26, from which reservoirs 32 and 34 the substances 28 and 30 can be respectively pumped into the chambers 22 via a three-way valve 40. This pumping is accomplished by operating one of allocated, manually actuated pumps 36 and 38. Instead, it would also be possible to insert a single pump into the feeder from the three-way valve 40 to the chambers 22. In the embodiment shown in the drawing, however, the reservoirs 32 and 34 are respectively implemented as a part of the pump 36 or 38 as a unitary structural component. The pumps 36 and 38 respectively have pistons 42 and 44, whereby the piston 42 is arranged movable (indicated with a double arrow 46) in the reservoir 32 by means of a manual drive and the piston 44 is arranged movable (indicated with a double arrow 48) in the reservoir 34 by means of a further manual drive. The dimensions of the reservoirs 32 or 34 are variable by operation of the pistons 42 and 44.

In employment, the chambers 22 are filled, for example, with the first substance 28 before the production of a first tomogram, whereby the three-way valve 40, as shown, opens the connection between the reservoir 32 and the chamber 22 and the piston 42 manually depresses to discharge the substance 28 into the chamber 22. After the first tomogram has been produced, the first substance 28 is in turn extracted from the chambers 22 by manually withdrawing the piston 42. After a quarter revolution of the three-way valve 40, the chambers 22 can be filled with the second substance 30 before producing the second tomogram by repeating this procedure with the reservoir 34 and the piston 44. The chambers 22 and the reservoirs 38 and 38 remain in uninterrupted fluid connection via the valve 40, during the production of the MR tomograms. "Uninterrupted" as used herein means that there is no need to remove one reservoir and to replace it with another during the production of MR images. Since the two substances behave differently in terms of magnetic resonance and are thus shown in different brightness and with different contrast from the environment in the two tomograms, the marking information is visible in both the individual images as well as the subtraction image. Important tissue sections can thus be localized with the assistance of the marks in the individual images and in the subtraction image.

Although modifications and changes may be suggested by those skilled in the art, it is the intention of the inventor to embody within the patent warranted hereon all changes and modifications as reasonably and properly come within the scope of her contribution to the art.

I claim as my invention:

1. A stereotactic examination arrangement for a magnetic resonance imaging apparatus, said arrangement comprising:

holder means for fixing an examination subject in an examination space;

antenna means for receiving magnetic resonance signals from said examination subject in said examination space, said antenna means having a detection region encompassing said examination space;

marker means disposed in said detection region, and having at least one chamber containing a fluid, for producing a mark visible in a magnetic resonance image of said examination subject generated from said magnetic resonance signals obtained by said antenna means; and refilling means, in uninterrupted fluid connection with said at least one chamber, for selectively filling said chamber with one of first and second fluids, said first and second fluids having respectively different magnetic resonance behavior.

2. A stereotactic examination arrangement as claimed in claim 1 wherein said marker means is connected to said holder means.

3. A stereotactic examination arrangement as claimed in claim 1 wherein said refilling means comprises:

a reservoir for said first fluid; and a pump in fluid communication with said reservoir for filling said at least one chamber with said first fluid and emptying said first fluid from said at least one chamber.

4. A stereotactic examination arrangement as claimed in claim 3 wherein said refilling means further comprises:

a further reservoir for said second fluid; and a further pump in fluid communication with said further reservoir for filling said at least one chamber with said second fluid and emptying said second fluid from said at least one chamber.

5. A stereotactic examination arrangement as claimed in claim 4 wherein said further reservoir and said further pump comprise a unitary structure.

6. A stereotactic examination arrangement as claimed in claim 5 wherein said further pump comprises a piston removably disposed in an interior of said further reservoir for varying a volume of said interior of said further reservoir.

7. A stereotactic examination arrangement as claimed in claim 3 wherein said pump and said reservoir comprise a unitary structure.

8. A stereotactic examination arrangement as claimed in claim 7 wherein said pump comprises a piston movably disposed in an interior of said reservoir for varying a volume of said interior of said reservoir.

9. A stereotactic examination arrangement as claimed in claim 1 wherein said holder means comprises two compression plates and means for moving said compression plates toward and away from each other.

10. A stereotactic examination arrangement as claimed in claim 9 wherein said marker means comprises two chambers with one chamber disposed on each said compression plate, and said refilling means comprising fluid lines connected to each of said chambers.

11. A stereotactic examination arrangement as claimed in claim 1 wherein said holder means comprises means for holding an examination subject for conducting a biopsy of said examination subject.

12. A stereotactic examination arrangement as claimed in claim 11 wherein said holder means comprises a plurality of through-holes adapted for guided access of a biopsy needle to said examination space from an exterior of said holder means.

13. A stereotactic examination arrangement as claimed in claim 1 further comprising a housing containing said holder means and said antenna means, said housing having an opening therein providing access to said examination space.

14. A stereotactic examination arrangement for a magnetic resonance imaging apparatus, said arrangement comprising:

holder means for fixing an examination subject in an examination space;

antenna means for receiving magnetic resonance signals from said examination subject in said examination space, said antenna means having a detection region encompassing said examination space associated therewith;

marker means disposed in said detection region, and having at least one chamber containing a fluid, for producing a mark visible in a magnetic resonance image of said examination subject generated from said magnetic resonance signals obtained by said antenna means; and refilling means, for successively filling and emptying said at least one chamber with a first fluid and a second fluid, said refilling means comprising a first reservoir containing said first fluid, a second reservoir containing said second fluid, valve means in fluid communication with said first reservoir, said second reservoir and said at least one chamber for selectively placing one of said first reservoir or said second reservoir in fluid communication with said at least one chamber, first pumping means in fluid communication with said first reservoir for filling said at least one chamber with said first fluid and emptying said first fluid from said at least one chamber when said first reservoir is in fluid communication with said at least one chamber via said valve means, and second pumping means in fluid communication with said second reservoir for filling said at least one chamber with said second fluid and emptying said second fluid from said at least one chamber when said second reservoir is in fluid communication with said at least one chamber via said valve means.

15. A stereotactic examination arrangement as claimed in claim 14 wherein said marker means is connected to said holder means.

16. A stereotactic examination arrangement as claimed in claim 14 wherein said first reservoir and said first pump means comprise a first unitary structure and wherein said second reservoir and said second pump means comprise a second unitary structure.

17. A stereotactic examination arrangement as claimed in claim 16 wherein said first pump means comprises a first piston movably disposed in an interior of said first reservoir for varying a volume in the interior of said first reservoir and wherein said second pump means comprises a piston movably disposed in an interior of said second reservoir for varying a volume in the interior of said second reservoir.

18. A stereotactic examination arrangement as claimed in claim 14 wherein said holder means comprises two compression plates and means for moving said compression plates toward and away from each other.

19. A stereotactic examination arrangement as claimed in claim 18 wherein said marker means comprises two chambers with one chamber disposed on each said compression plate, and said refilling means comprising fluid lines connected to each of said chambers.

20. A stereotactic examination arrangement as claimed in claim 14 wherein said holder means comprises means for holding an examination subject for conducting a biopsy of said examination subject.

21. A stereotactic examination arrangement as claimed in claim 20 wherein said holder means comprises a plurality of through-holes adapted for guided access of a biopsy needle to said examination space from an exterior of said holder means.

22. A stereotactic examination arrangement as claimed in claim 14 further comprising a housing containing said holder means and said antenna means, said housing having an opening therein providing access to said examination space.

* * * * *